(12) United States Patent
Mennenga et al.

(10) Patent No.: US 8,408,078 B2
(45) Date of Patent: Apr. 2, 2013

(54) APPARATUS FOR REMOVING SAMPLES FROM SYSTEMS HAVING FLEXIBLE WALLS AND FOR INTRODUCING FLUIDS INTO THE SAME

(75) Inventors: Heyo Mennenga, Rostock (DE); Oscar-Werner Reif, Hanover (DE); Dieter Schmidt, Rosdorf (DE); Reinhard Vogt, Dransfeld (DE)

(73) Assignee: Sartorius Stedim Biotech GmbH (DE)

( * ) Notice: Subject to any disclaimer, the term of this patent is extended or adjusted under 35 U.S.C. 154(b) by 464 days.

(21) Appl. No.: 11/713,978

(22) Filed: Mar. 5, 2007

(65) Prior Publication Data

US 2007/0227270 A1   Oct. 4, 2007

(30) Foreign Application Priority Data

Mar. 29, 2006   (DE) .......................... 10 2006 014 495

(51) Int. Cl.
*G01N 1/02* (2006.01)
*G01N 1/10* (2006.01)
(52) U.S. Cl. .................... 73/863.85; 73/863.82
(58) Field of Classification Search ... 73/863.81–863.85
See application file for complete search history.

(56) References Cited

U.S. PATENT DOCUMENTS

| | | | | |
|---|---|---|---|---|
| 2,955,595 A * | 10/1960 | Semple | ......................... | 600/573 |
| 3,354,881 A * | 11/1967 | Bloch | .......................... | 604/198 |
| 4,988,341 A * | 1/1991 | Columbus et al. | ............ | 604/306 |
| 5,122,123 A * | 6/1992 | Vaillancourt | .................. | 604/192 |
| 5,267,972 A * | 12/1993 | Anderson | ...................... | 604/192 |
| 5,465,768 A * | 11/1995 | DeRoos et al. | ............ | 73/864.63 |
| 5,591,138 A * | 1/1997 | Vaillancourt | .................. | 604/263 |
| 5,885,255 A * | 3/1999 | Jaeger et al. | .................. | 604/192 |
| 6,162,206 A * | 12/2000 | Bindokas et al. | ............. | 604/533 |
| 6,845,676 B2 * | 1/2005 | Bigalke | ..................... | 73/863.85 |
| 6,884,224 B2 * | 4/2005 | Dalton | ......................... | 600/573 |
| 7,219,874 B2 * | 5/2007 | Tippett | ......................... | 251/89.5 |
| 7,297,136 B2 * | 11/2007 | Wyrick | ......................... | 604/117 |
| 2007/0269350 A1* | 11/2007 | Coyne et al. | .................. | 422/102 |

* cited by examiner

*Primary Examiner* — Hezron E Williams
*Assistant Examiner* — Nashmiya Fayyaz
(74) *Attorney, Agent, or Firm* — Gerald E. Hespos; Michael J. Porco; Matthew T. Hespos

(57) ABSTRACT

The invention discloses an apparatus for removing samples or introducing fluids from/into system(s) having flexible walls. A sampler/fluid dispenser (3) is fixed on the outside with a connecting area (4) of its base (5) on a sample removal region/fluid dispensing region (6) of the flexible wall (2) and, in its interior, has a severing element (8). At least the severing element (8) can be pushed forward in the direction of the sample removal region/fluid dispensing region (6) in order to remove the samples and in order to introduce fluids, in such a way that the wall (2) can be perforated within the sample removal region/fluid dispensing region (6). The system (1) comprises containers, bags or tubes for filling, mixing, transporting, storage of media, such as biological liquids, sera, buffers, ultra-pure water and can be used as biological reactors or cell culture vessels in the pharmaceutical and biotechnical industry.

7 Claims, 2 Drawing Sheets

APPARATUS FOR REMOVING SAMPLES FROM SYSTEMS HAVING FLEXIBLE WALLS AND FOR INTRODUCING FLUIDS INTO THE SAME

BACKGROUND OF THE INVENTION

1. Field of the Invention

The invention relates to an apparatus in the form of a unit comprising a system with flexible walls, such as containers, bags and tubes, and a sampler for removing samples from the system and for introducing fluids into the systems.

2. Description of the Related Art

One of the current trends in biological processing and pharmaceutical engineering is the increasing use of internally sterile flexible disposal systems. The walls of these systems isolate the inner sterile environment from the outer, largely unsterilized, environment (sterile barrier). When such systems are used, no germs may get from the outside to the inside or from the inside to the outside.

"Sterile system" here is used in the sense that this system is sterile before use and, on account of its design, during use permits no germs to get from the outside into the interior of the system.

One problem when using such systems is the removal of samples from the flexible sterile disposable systems. In the case of blood bags, as the best-known example of sterile, flexible disposable systems, it is known to use a tube that is connected to the sterile interior and closed on the other side, to empty said tube with roller tongs then, with the expansion of the tube after the roller tongs have been removed, to allow the latter to fill with the liquid to be tested, then at the end of the tube to fuse off a piece of tube with two welds located beside each other and to cut through the tube between the welds. The result is a small sample volume in a piece of tube closed securely on both sides. Here, the restriction to very small sample volumes is disadvantageous. Sampling systems such as are used on steel reactors are not known for flexible systems. These have the disadvantage that, for use in conjunction with biological reactors, they are complicated to sterilize, wholly or partly, preferably by means of steam.

The object of the invention is to specify an apparatus for removing samples from systems and for introducing fluids into systems having flexible walls which meets requirements for purity and requires little expenditure for the production and the use of the apparatus.

SUMMARY OF THE INVENTION

The object is achieved by an apparatus in the form of a unit comprising a system having flexible walls and at least one sampler for removing samples from the system and for introducing fluids into the system.

For the purpose of improved clarity and for linguistic simplicity, only the term "sampler" will be used. However, this is to be understood to mean to both a sampler for removing samples from the system and a fluid dispenser for introducing fluids into the system.

The sampler is fixed on the outside with a connecting area of its base in a fluid tight manner on a sample removal region of the flexible wall and has a severing element in its interior.

For the purpose of improved clarity and for linguistic simplicity, only the term "sample removal region" will be used. However, this is to be understood to mean to both a sample removal region for removing samples from the system and a fluid dispensing region for introducing fluids into the system.

At least the severing element can be pushed forward in the direction of the sample removal region in order to remove the samples in such a way that the wall within the sample removal region is perforated in the process, so that there is a communicating connection between the interior of the system and the sampler. The severing element can be pushed forward by hand, for example, the severing element advantageously being enclosed by an elastic sleeve, for example one like a bellows.

In a preferred embodiment of the invention, the system and its sampler are internally sterile and the sample removal region and the connecting area are designed to be germ free. To this end, for example, the sample removal region and the connecting area of the base of the sampler are pre-sterilized and, for example, covered with a protective film that can be pulled off, which is removed only as they are joined together. The sterilization of the outside of the sample removal region of the flexible wall can be carried out, for example, over a large area by means of treatment with sterilizing agents.

The sampler advantageously has on its base a septum which is connected to the flexible wall. In this case, a shank part of the septum or the base of the sampler can be elastic, which means that, in order to remove the samples, the severing element can be pushed forward in the direction of the sample removal region in such a way that the wall of the system can be perforated, so that a communicating connection is produced between the interior of the system and the sampler.

The connection comprising septum, flexible wall and connecting layer between septum and wall is designed in such a way that it can be perforated by the severing element. For example, plungers, hollow needles or dual cannulae which have points and/or cutting edges can be used as the severing element. The use of dual cannulae is preferred if the walls of the systems are relatively inflexible or if relatively large sample quantities are to be removed quickly or relatively large quantities of fluid are to be introduced quickly. By one of the cannulae in the dual cannula, a gas is introduced into or removed from the system for the purpose of pressure compensation for the sample quantity removed or for the quantity of fluid supplied, said gas for example being filtered in a sterile manner via a hydrophobic sterile filter for gases before entering this cannula or before leaving the cannula. This ensures that contamination of the interior of the system and of the sampler and also of the environment is avoided. A collecting vessel as a sample collector, or a supply vessel for fluids to be introduced, for example in the form of a sample/fluid container and/or sampler/fluid dispenser tube, can be connected to the sampler. A vacuum can be applied to these for the purpose of an improved ability to fill with samples, or a positive pressure can be applied to make it easier to introduce a fluid into the system, or they have a communicating connection with the atmosphere in order to remove samples via a sterile filter for gases.

In one embodiment of the invention, the connection to the connecting area is carried out by means of a sterilizing adhesive. In a further embodiment, the connection to the connecting area can be produced by means of softening and solidifying plastic, at least of the wall and/or of the base of the sampler. The softening can be carried out thermally or by means of solvents.

In order to ensure adequate stability of the connection in the case of small systems whose walls have a sharp curvature, the base of the sampler or else the shape of the septum is matched to the outer contour of the flexible wall in the sample removal region.

The systems having the flexible walls preferably comprise a container with a varying external shape, such as a canister, a bag and/or a tube. The systems can be used, for example, as vessels for filling, mixing, transporting, storing media, such as biological fluids, sera, buffers, ultra-pure water or the like. They can also be used as biological reactors or cell culture vessels. They are used in particular in the pharmaceutical, chemical, biotechnical industry and in gene and medical technology.

The apparatus can also be sterilized only when in the form of the unit comprising the system with flexible walls and the sampler, that is to say following the production of the fluid tight fixing of the sampler to the sample removal region of the system, for example sterilized by means of the action of gamma radiation, by means of electronic radiation or in another way, for example by the action of heat. As a result, the system having the flexible wall and the sampler is sterile on the inside. For the purpose of use, i.e., if a sample is to be removed from the interior of the flexible system during a process step, for example the hollow needle of the sampler is pushed forward as far as the interior of the flexible system, the wall being pierced, and then the liquid sample to be examined flows through the needle into a collecting vessel, which is preferably under vacuum at the start of the sample removal. A sampler tube can be present on the collector, or it is fitted directly to the sampler. Following the removal of the sample, the tube can repeatedly be sealed off by means of clamping, including the use of a metal clamp, or by welding, and separated between the sealed points. In this way, a sample of any desired size can be removed in a sterile manner and subjected to examination.

A plurality of such samplers can be fixed to the flexible system, so that a plurality of samples can also be removed in an isolated manner or a plurality of fluids can be supplied in an isolated manner.

The subject according to the invention can also be applied to the removal of sample quantities from tubes and for the introduction of fluids into tubes, for which purpose the area to be pierced is connected tightly to the wall of the tube and tube and sampler are sterilized together. During the sample removal, septum, connecting layer and tube wall are pierced.

DETAILED DESCRIPTION OF THE PREFERRED EMBODIMENTS

Figure 1A:
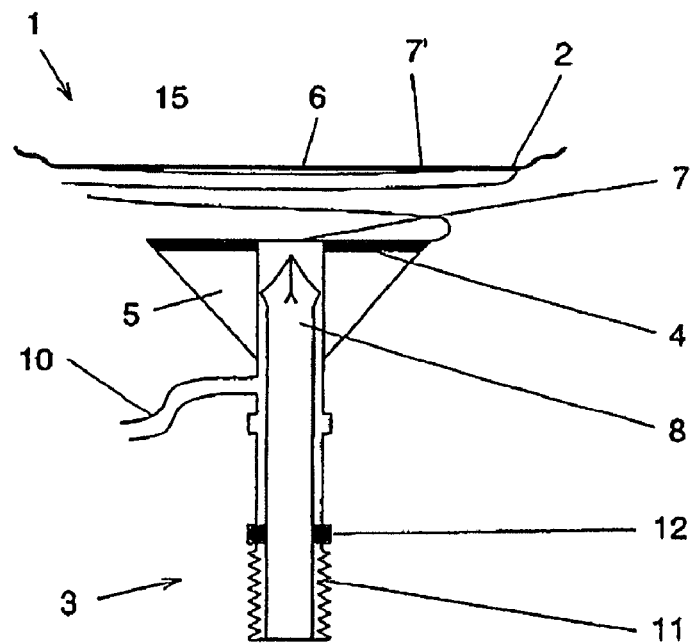
FIG. 1a shows an extract from a system having flexible walls and a sampler in the isolated state.
Figure 1B:
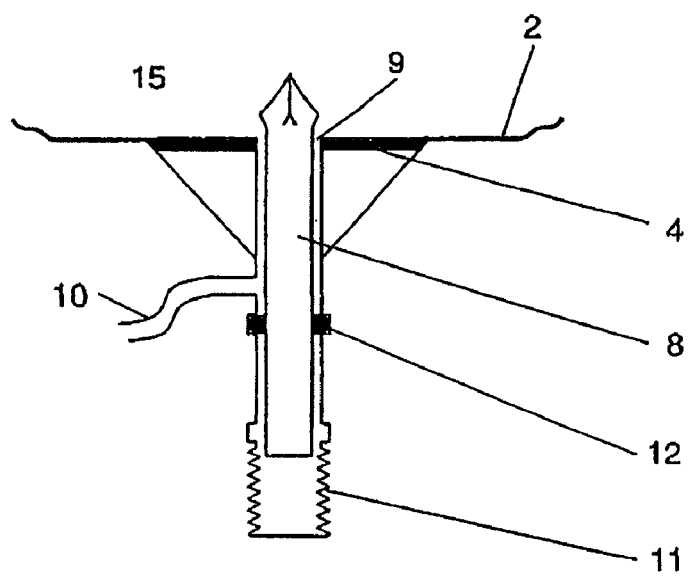
FIG. 1b shows an extract from a system having flexible walls and a sampler in the sample removal state.

FIGS. 1a and 1b show a system 1 having a flexible wall 2 and a sampler 3 for the removal of samples from the system and for the introduction of fluids into the system. The sampler 3 has a connecting area 4 on its base 5. The base can be fixed (FIG. 1a) or is fixed (FIG. 1b) on the outside in a fluid tight manner on a sample removal region 6 of the flexible wall 2. The connecting area 4 and the sample removal region 6 can be protected, as shown in FIG. 1a, by protective films 7, 7' that can be pulled off before they are joined together.

The sampler 3 has a severing element 8 in its interior. The severing element 8 can be moved in the direction of the sample removal region 6, specifically in such a way that the wall 2 within the sample removal region 6 can be perforated by the severing element 8, so that there is a communicating connection 9 between the interior of the system 1 and a sampler 3, by which connection the sample can be transferred into a sampler tube 10 or a fluid from a storage vessel can be introduced into the system. The severing element 8, which is formed as a plunger in the embodiment of FIGS. 1a/1b, can be moved by means of a sheath 11 like a bellows. Provided on the shank of the plunger is a seal 12 which, at the same time, forms a type of locking means.

Figure 2:
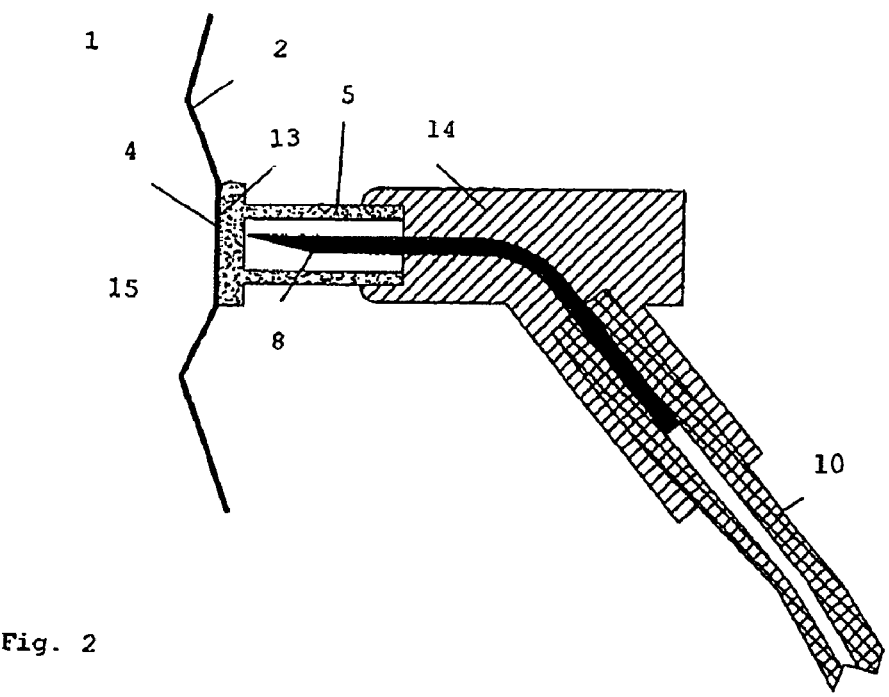
FIG. 2 shows a further apparatus according to the invention having a bag.

Part of the flexible wall 2 of an internally sterile system (bag) 1 is illustrated in FIG. 2. The sampler comprises a sharp hollow needle as a severing element 8, a soft and flexible septum 13 formed as the base 5 of the sampler, and a hard handheld part 14, in which part of the hollow needle 8 and a sampler tube 10 adjoining the hollow needle are embedded. The sampler tube can also be used as a connecting tube to a sterile collecting vessel (collector), not illustrated, for the sample or, respectively, a supply vessel for fluids to be introduced. A part of the septum 13 to be pierced is welded, adhesively bonded or connected firmly and in a fluid tight manner in another way to a sample removal region 6 of the bag wall 2 via a connecting area 4.

Following the production of this connection, bag 1 and sampler 3 are sterilized together. It is possible to dispense with the joint sterilization if bag and sampler are sterilized separately and then connected according to the invention in such a way that the connecting area 4 is germ free as a result of the connecting step. This can be done, for example, by means of thermal welding, for example mirror welding, at least one side being softened thermally, or with an adhesive that is effective for organic polymers and which acts in a completely disinfecting manner. In order to remove a sample and to introduce fluids, the handheld part 4 is gripped and, using this part, the hollow needle 8 is pushed through septum 13 and bag 2 into the sterile interior 15 of the bag. In this way, a sterile communicating connection 9 (not illustrated) suitable for the passage of a fluid (liquid, gas) is produced from the interior of the flexible system 1 via the interior of the sampler 3 to the collecting container or, respectively, to the supply vessel for fluids.

Figure 3:
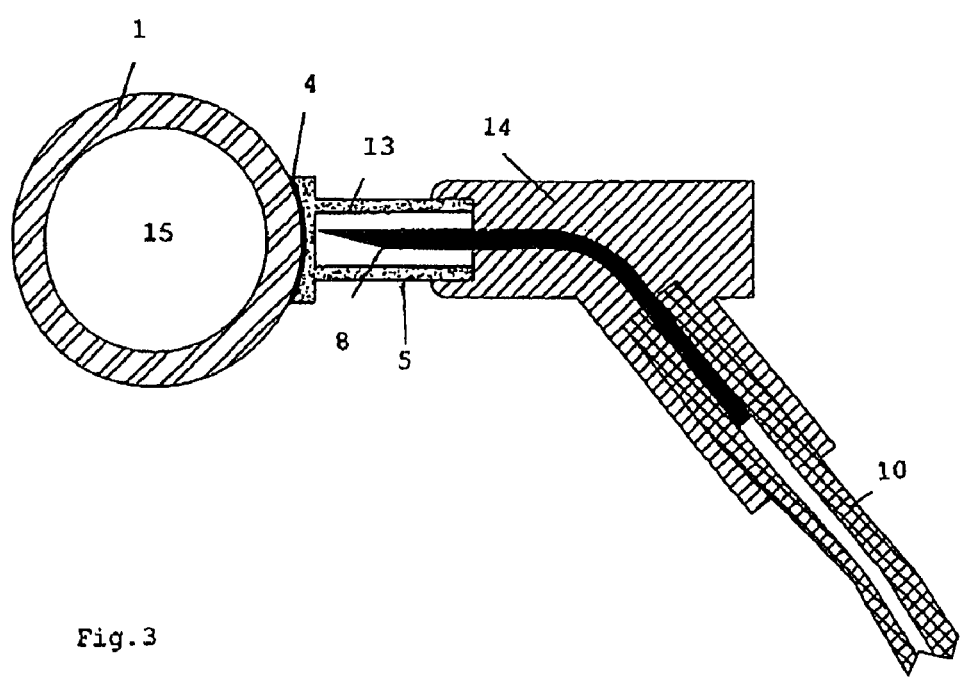
FIG. 3 shows a further apparatus according to the invention having a tube.

A tube is illustrated in FIG. 3 as an example of a sterile flexible system 1 from whose sterile interior 15 a sample is to be removed or into whose sterile interior a fluid is to be introduced. The septum 13 of the sampler 3 is connected tightly and firmly to the outer wall 2 of the tube 1 with the connecting area 4 on a sample removal region 6. The shape of the septum 13 is beneficially matched to the outer diameter of the tube 1 for this purpose. During the sample removal, septum 13, connecting area 4 and tube wall 2 are pierced.

List of Designations

1 System
2 Flexible wall
3 Sampler/fluid dispenser
4 Connecting area
5 Base
6 Sample removal region/fluid introduction region
7 Protective films
8 Severing element
9 Communicating connection
10 Sampler tube
11 Bellows-like sheath
12 Seal
13 Septum 14 Handheld part
15 Interior of the system

What is claimed is:

1. Apparatus for removing samples from a system (1) having at least one flexible wall (2) and for introducing fluids into the system (1), the apparatus comprising:
    at least one sampler/fluid dispenser (3) that includes a hard part (14) having opposite front and rear ends;
    a severing element (8) having an intermediate region mounted in the hard part (14) and a severing end projecting from the front end of the hard part (14), the intermediate region of the severing element (8) being bent angularly relative to the severing end, a sampling tube (10) being connected to an end of the severing element (8) opposite the severing end and extending angularly from the hard part (14) at a position between the front and rear ends of the hard part (14); and
    a substantially tubular base (5) with an open end mounted to the hard part (14) at locations spaced outward from the severing element (8) so that the open end of the substantially tubular base (5) is spaced from the severing element (8), the substantially tubular base (5) further having a closed connecting area (4) remote from the hard part (14) and configured to fix the sampler/fluid dispenser (3) in a fluid tight manner on a sample removal region/fluid dispensing region (6) defined on an outer side of the wall (2) of the system (1), portions of the tubular base (5) between the open end and the closed connecting area (4) being spaced outward from the severing element (8) and being elastic and radially unconfined, the base (5) of the sampler/fluid dispenser (3) being formed as a septum (13), the septum (13) being flexible so that the shape of the septum (13) matches an outer contour of the flexible wall (2) in the sample removal region/fluid dispensing region (6) and so that a pushing of the hard part (14) toward the sample removal region/fluid dispensing region (6) causes the severing element (8) to move through the flexible septum (13) and into an interior of the system (1).

2. Apparatus according to claim 1, wherein system (1) and the sampler/fluid dispenser (3) are internally sterile and the sample removal region/fluid dispensing region (6) and the connecting area (4) are germ free.

3. Apparatus according to claim 1, further comprising a removable protective film covering the connecting area (4).

4. Apparatus according to claim 1, wherein the system (1) comprises at least one bag and/or tube.

5. Apparatus according to claim 1, wherein the fixing to the connecting area (4) is implemented by means of a sterilizing adhesive.

6. Apparatus for sterile transfer of liquid sample, comprising:
    a system (1) having at least one flexible wall (2) defining a sterile interior for the system (1), the flexible wall (2) having a sample removal region/fluid dispensing region (6) on an outer surface of the flexible wall (2);
    a flexible tubular septum (13) having a closed end defining a connecting area (4) fixedly connected on the outer surface of the sample removal region/fluid dispensing region (6) in substantially face-to-face contact and in a fluid tight manner, the flexible tubular septum (13) further having an open end opposite the closed end, a mounting area adjacent the open end and a flexible tubular part extending from the mounting area to the connecting area (4);
    a hard handheld part (14) having opposite front and rear ends, the front end of the hard handheld part (14) being mounted over the mounting area and the open end of the flexible tubular septum (13) so that the tubular part of the flexible tubular septum (13) extends from the hard handheld part (14) to the connecting area (4) and is radially unconfined; and
    a severing element (8) having an intermediate portion embedded in the hard handheld part (14) and a leading end projecting from the front end of the hard handheld part (14) toward the connecting area (4) of the flexible tubular septum (13), the intermediate portion of the severing element (8) being bent angularly relative to the leading end, a sampling tube (10) being connected to a rear end of the severing element (8) and extending angularly from the hard handheld part (14) at a position between the front and rear ends of the hard handheld part (14), the severing element (8) being spaced inwardly from the flexible tubular septum (13) at locations on the flexible tubular septum (13) connected to the hard handheld part (14), wherein a pushing of the hard handheld part (14) toward the sample removable region/fluid dispensing region (6) causes the leading end of the severing element (8) to move through the connecting area (4) of the flexible tubular septum (13) and through the sample removal region/fluid dispensing region (6) to which the connecting area (4) is fixedly connected.

7. The apparatus of claim 6, further comprising a sterilizing adhesive connecting the flexible tubular septum (13) to the sample removal region/fluid dispensing region (6) in a fluid tight manner.

* * * * *